United States Patent [19]

Karni

[11] Patent Number: 5,655,547
[45] Date of Patent: Aug. 12, 1997

[54] METHOD FOR LASER SURGERY

[75] Inventor: Ziv Karni, Kfar Shemaryahu, Israel

[73] Assignee: ESC Medical Systems Ltd., Yokneam, Israel

[21] Appl. No.: 647,531

[22] Filed: May 15, 1996

[51] Int. Cl.$^6$ ................................................. A61B 19/00
[52] U.S. Cl. ................................. 128/898; 606/3; 606/9; 606/16
[58] Field of Search ........................ 606/3, 9, 10, 5, 606/2, 11–12, 15, 16; 128/898

[56] References Cited

U.S. PATENT DOCUMENTS

| | | |
|---|---|---|
| 3,710,798 | 1/1973 | Bredemeier . |
| 4,408,602 | 10/1983 | Nakajima . |
| 4,454,882 | 6/1984 | Takano . |
| 4,503,854 | 3/1985 | Jako . |
| 4,520,816 | 6/1985 | Schachar et al. . |
| 5,084,881 | 1/1992 | Farries et al. . |
| 5,139,494 | 8/1992 | Freiberg . |
| 5,290,274 | 3/1994 | Levy et al. . |
| 5,387,211 | 2/1995 | Saadatmanesh et al. . |

OTHER PUBLICATIONS

Kaufman, R., "Pulsed Erbium: YAG Laser Ablation in Cutaneous Surgery", partly presented at 15th Annual Mtg of the American Society for Laser Medicine and Surgery, Apr., 1995.

*Primary Examiner*—Vincent Millin
*Assistant Examiner*—Kelly R. O'Hara
*Attorney, Agent, or Firm*—Mark M. Friedman

[57] ABSTRACT

A method of laser surgery, comprising the steps of selecting lasers whose output radiation has appropriate extinction lengths in the tissue to be ablated, coagulated, and/or shrunk, and directing radiation from those lasers coaxially and substantially simultaneously at the tissue.

22 Claims, 2 Drawing Sheets

METHOD FOR LASER SURGERY

FIELD AND BACKGROUND OF THE INVENTION

The present invention relates to a method for performing laser surgery and, more particularly, to a method for simultaneously ablating, coagulating, and/or shrinking biological tissue.

Directing coherent radiation from a laser at a target is a well known method for precisely cutting that target by ablating or vaporizing a portion of it. When the target is living biological tissue, the dynamic nature of the target poses special problems. For example, fluids such as blood may flow into the area of the cut, obscuring that area and absorbing part of the energy that otherwise would go into ablating the target.

This problem can be mitigated by directing beams of coherent radiation of two or more wavelengths at the tissue, one beam to ablate the tissue and the other to perform some other action, such as coagulating small blood vessels to prevent inflow of blood. For example, Freiberg, in U.S. Pat. No. 5,139,494, which is incorporated by reference for our purposes as if fully set forth herein, advocates using radiation in a range of wavelengths between about 0.1 and about 0.3 microns, and between about 2.0 and about 12.0 microns, for ablative cutting, and radiation in a range of wavelengths between about 0.3 microns and about 2.0 microns for coagulation. These beams of coherent radiation are directed coaxially at the tissue to be cut. Suitable means for combining laser beams coaxially are well known in the art. One such means is disclosed by Nakajima in U.S. Pat. No. 4,408,602. Another is disclosed by Jako in U.S. Pat. No. 4,503,854. Both of these patents are incorporated by reference for all purposes as if fully set forth herein.

Among the surgical procedures, to which laser surgery may be applied are skin resurfacing and hair implantation. In skin resurfacing, the upper layer of skin is ablated by a first laser beam while the underlying collagen is coagulated and shrunk by a second laser beam. In hair implantation, the accuracy of the drilling of holes for the implantation of new hair using a first laser beam is enhanced by the use of a second laser beam to coagulate small blood vessels and prevent inflow of blood. Both of these procedures are very delicate and require precise selection and control of the wavelengths, intensities and durations of the laser beams.

There is thus a widely recognized need for, and it would be highly advantageous to have, a more precise method for using lasers to perform delicate surgical procedures such as skin resurfacing and hair implantation.

SUMMARY OF THE INVENTION

According to the present invention there is provided a method for surgical alteration of skin tissue by simultaneous ablation, coagulation, and shrinkage, comprising the steps of: (a) selecting a first coherent radiation source characterized by emitting a first coherent radiation having an extinction length in the skin tissue of between about 0.01 millimeters and about 0.001 millimeters; (b) selecting a second coherent radiation source characterized by emitting a second coherent radiation having an extinction length in the skin tissue of between about 0.1 millimeters and about 0.01 millimeters; (c) directing a first beam of the first coherent radiation at the skin tissue; and (d) directing a second beam of the second coherent radiation at the skin tissue, substantially coaxially and substantially simultaneously with the first beam.

According to the present invention there is provided a method for surgical alteration of skin tissue by simultaneous ablation, coagulation, and shrinkage, comprising the steps of: (a) selecting a first coherent radiation source characterized by emitting a first coherent radiation having an extinction length in the skin tissue of between about 0.01 millimeters and about 0.001 millimeters; (b) selecting a second coherent radiation source characterized by emitting a second coherent radiation having an extinction length in the skin tissue of between about one millimeter and about 0.1 millimeters; (c) directing a first beam of the first coherent radiation at the skin tissue; and (d) directing a second beam of the second coherent radiation at the skin tissue, substantially coaxially and substantially simultaneously with the first beam.

The criteria for selecting the parameters for delicate laser surgery on skin tissue are the desired physical effects. The ablative laser beam should be strongly absorbed by the target tissue, so that the ablative effects of the laser beam are confined to the target tissue. Furthermore, the pulse duration should be shorter than the thermal relaxation time of the target tissue, to prevent thermal damage to adjacent tissue, while the pulse intensity should be sufficiently high to achieve the desired ablation. In skin resurfacing, the laser beam used to shrink the collagen should not be significantly absorbed in the overlying skin, but should be absorbed by the collagen. In hair implantation, the laser beam used should be absorbed only to an extent sufficient to coagulate the capillaries that are cut by the ablative laser beam.

The present invention successfully addresses the shortcomings of the presently known procedures for skin resurfacing and hair implantation by providing an appropriate range of wavelengths, pulse durations, and pulse intensities for the laser beams used therein.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a method for delicate laser surgery. Specifically, the present invention can be used for precision skin resurfacing and hair implantation.

The principles of precision laser surgery according to the present invention may be better understood with reference to the drawings and the accompanying description.

Figure 1:
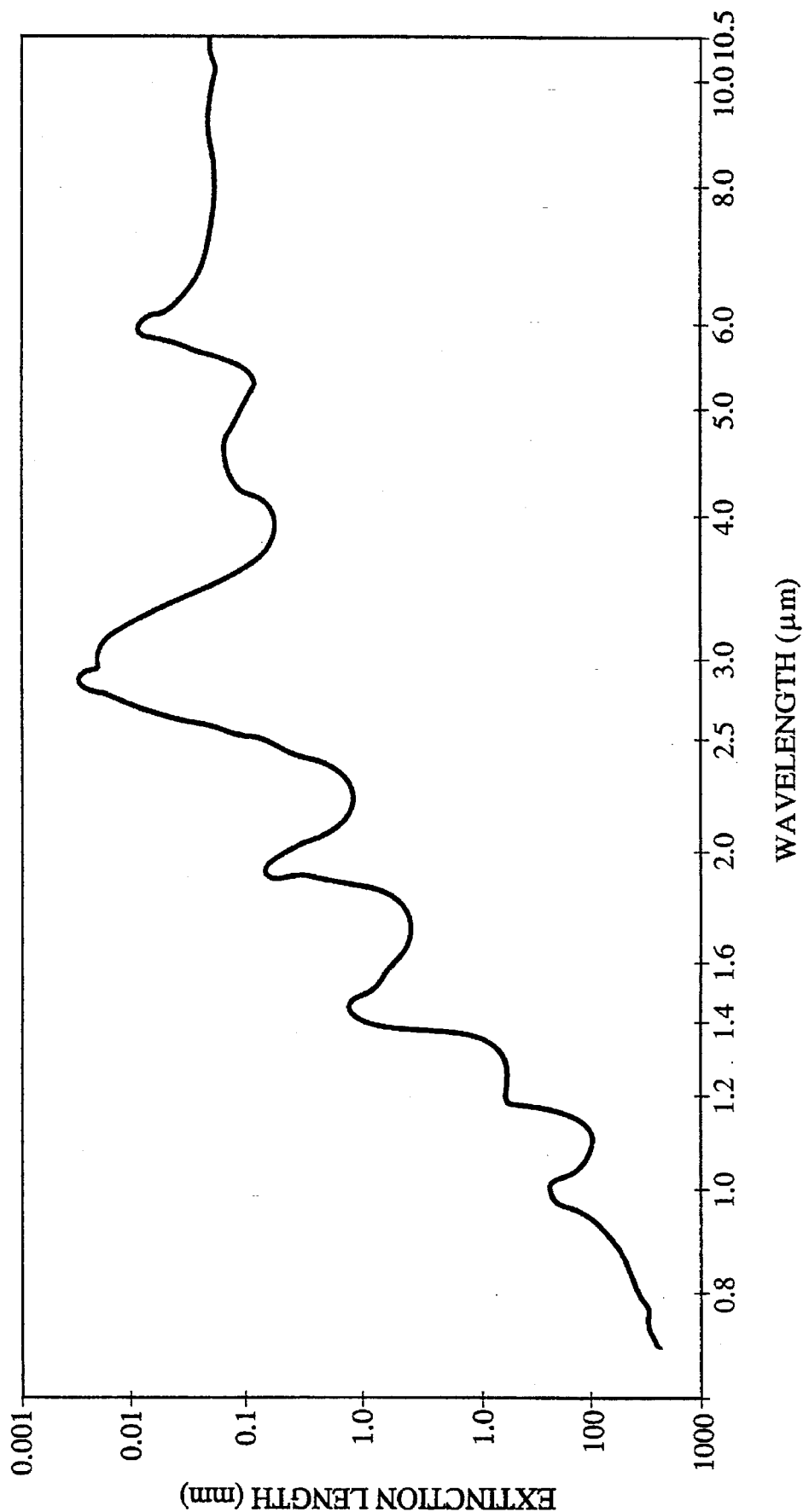
FIG. 1 is a graph of the extinction length, in water, of light of various wavelengths, vs. wavelength.

Referring now to the drawings, FIG. 1 is a graph of the extinction length in water of infrared radiation of various wavelengths. Because skin tissue is 77% water by weight, water can be used as a proxy for skin tissue in selecting wavelengths for surgery.

To minimize peripheral damage, the extinction length of coherent radiation used for ablative cutting should be as small as possible. According to FIG. 1, this length is between 0.01 millimeters and 0.001 millimeters. Note that the corresponding range of wavelengths is between about 2.5 microns and about 3.2 microns. This range is substantially narrower than the 2–12 micron range recommended by Freiberg for ablative cutting. The 2.94 micron radiation of an erbium YAG laser has an extinction length in this range. The thermal relaxation time of human skin tissue is approximately one millisecond. Thus, the laser pulse duration should be no longer than this, and preferably about 0.3 milliseconds. The energy density of each pulse preferably is between one Joule per square centimeter and 50 Joules per square centimeter.

The extinction length of coherent radiation used for coagulation of small blood vessels should be somewhat longer than the extinction length of coherent radiation used for ablation, to spread the heating effect of the laser beam over a larger depth range than is used for ablation. The intent here is merely to coagulate the blood, not to vaporize it. Between 0.1 millimeters and 0.01 millimeters is an appropriate extinction length for coagulation. The 10.6 micron radiation of a carbon dioxide laser has an extinction length in this range.

Figure 2A:
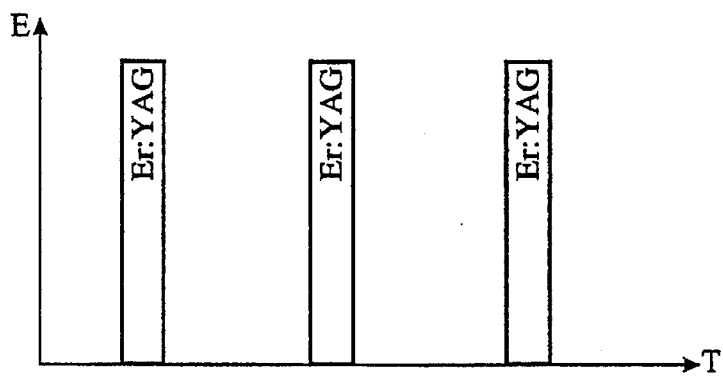
FIG. 2A shows the firing schedule of the lasers in one embodiment of the present invention.
Figure 2B:
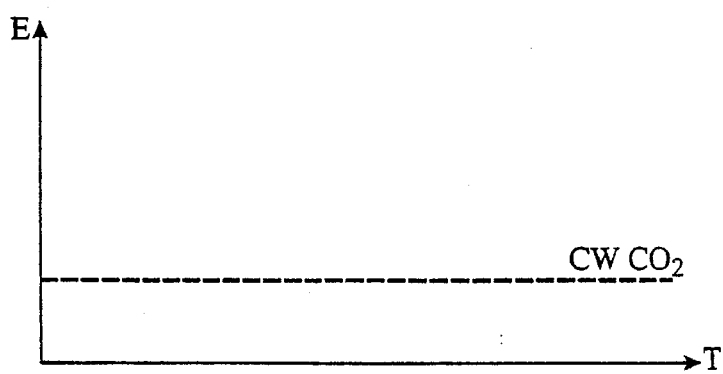
FIG. 2B shows the combined laser output corresponding to FIG. 2A.
Figure 2C:
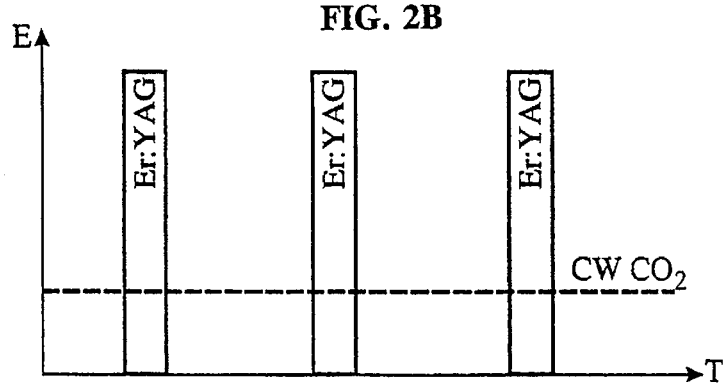
FIG. 2C shows the combined laser output corresponding to the firing schedule of a different embodiment of the present invention.

The laser beam used for coagulation may be either continuous or pulsed, as long as the duration of the coagulation beam substantially overlaps the duration of the ablation beam, as shown in FIGS. 2A, 2B, and 2C. In the four plots shown in these Figures, time T is the abscissa and beam intensity E is the ordinate. FIG. 2A shows separate firing schedules for an erbium YAG ablation laser and a carbon dioxide coagulation laser in a preferred embodiment of the present invention in which the carbon dioxide laser is a continuous wave laser. The erbium YAG laser emits periodic pulses. The carbon dioxide laser fires continuously. The total laser output is the superposition of these two outputs, as shown in FIG. 2B. Preferably, the power level of the carbon dioxide laser is sufficiently high to coagulate the blood vessels cut by the erbium YAG laser in between pulses of the erbium YAG laser, but not sufficiently high to cause peripheral damage by unwanted ablation. The preferred power density for a continuous wave carbon dioxide laser is between one Watt per square centimeter and 10 Watts per square centimeter.

FIG. 2C shows the combined output of the erbium YAG laser and the carbon dioxide laser in a preferred embodiment of the present invention in which both lasers are pulsed. Note that the duration of each carbon dioxide laser pulse overlaps, and extends substantially beyond, the duration of the corresponding erbium YAG laser pulse. Again, the object here is to coagulate the blood vessels cut by the erbium YAG laser without causing peripheral damage by unwanted ablation. The preferred carbon dioxide pulse duration is between one millisecond and 10 milliseconds, and the preferred power density is between one Watt per square centimeter and 100 Watts per square centimeter.

The extinction length of coherent radiation used to shrink collagen preferably should match the thickness of the target collagen layer, which may be as thick as about one millimeter. Collagen thinner than about 0.1 millimeters is shrunk by a laser appropriate for coagulation, for example a carbon dioxide laser. Thicker collagen is shrunk by a laser whose radiation has an extinction length of between about one millimeter and 0.1 millimeters. The 2.12 micron radiation of a holmium YAG laser has an extinction length in this range. The shrinkage laser beam may be continuous or pulsed. Preferred pulse durations for a holmium YAG laser used to shrink collagen are between 0.3 milliseconds and one millisecond, and the preferred pulse energy density is about one Joule per square centimeter.

The range of wavelengths useful for laser surgery, as shown in FIG. 1, is in the invisible infrared. In preferred embodiments of the present invention, a third, low power beam of visible coherent radiation is directed coaxially with the other two beams, so that the surgeon can see where the beams strike the patient.

While the invention has been described with respect to a limited number of embodiments, it will be appreciated that many variations, modifications and other applications of the invention may be made.

What is claimed is:

1. A method for surgical alteration of skin tissue by simultaneous ablation and coagulation, comprising the steps of:

(a) selecting a first coherent radiation source characterized by emitting a first coherent radiation having an extinction length in the skin tissue of between about 0.01 millimeters and about 0.001 millimeters;

(b) selecting a second coherent radiation source characterized by emitting a second coherent radiation having an extinction length in the skin tissue of between about 0.1 millimeters and about 0.01 millimeters;

(c) ablating the skin tissue by directing a first beam of said first coherent radiation at the skin tissue; and (d) coagulating the skin tissue by directing a second beam of said second coherent radiation at the skin tissue, substantially coaxially and substantially simultaneously with said first beam.

2. The method of claim 1, wherein said first coherent radiation source is a laser.

3. The method of claim 2, wherein said first coherent radiation source is an erbium YAG laser.

4. The method of claim 1, wherein said second coherent radiation source is a laser.

5. The method of claim 4, wherein said laser is a carbon dioxide laser.

6. The method of claim 1, wherein said first beam is pulsed.

7. The method of claim 6, wherein each of said pulses has a duration of about 0.3 milliseconds, and wherein each of said pulses has an energy density of between about one Joule per square centimeter and about 50 Joules per square centimeter.

8. The method of claim 6, wherein said second beam is continuous.

9. The method of claim 8, wherein said second beam has a power density of between about one Watt per square centimeter and about 10 Watts per square centimeter.

10. The method of claim 6, wherein said second beam is pulsed, said pulses of said second beam at least partially overlapping in time with said pulses of said first beam.

11. The method of claim 10, wherein each of said pulses of said second beam has a duration of between about one millisecond and about 10 milliseconds, and wherein each of said pulses of said second beam has a power density of between about one Watt per square centimeter and about 100 Watts per square centimeter.

12. The method of claim 1, further comprising the step of directing a third beam of visible coherent radiation at the skin tissue, substantially coaxially and substantially simultaneously with said first beam.

13. A method for surgical alteration of skin tissue by simultaneous ablation and shrinkage, comprising the steps of:

(a) selecting a first coherent radiation source characterized by emitting a first coherent radiation having an extinction length in the skin tissue of between about 0.01 millimeters and about 0.001 millimeters;

(b) selecting a second coherent radiation source characterized by emitting a second coherent radiation having an extinction length in the skin tissue of between about one millimeter and about 0.01 millimeters;

(c) ablating the skin tissue by directing a first beam of said first coherent radiation at the skin tissue; and (d) shrinking the skin tissue by directing a second beam of said second coherent radiation at the skin tissue, substantially coaxially and substantially simultaneously with said first beam.

14. The method of claim 13, wherein said first coherent radiation source is a laser.

15. The method of claim 14, wherein said first coherent radiation source is an erbium YAG laser.

16. The method of claim 13, wherein said second coherent radiation source is a laser.

17. The method of claim 16, wherein said laser is a holmium YAG laser.

18. The method of claim 13, wherein said first beam is pulsed.

19. The method of claim 18, wherein each of said pulses has a duration of about 0.3 milliseconds, and wherein each of said pulses has an energy density of between about one Joule per square centimeter and about 50 Joules per square centimeter.

20. The method of claim 18, wherein said second beam is pulsed, said pulses of said second beam at least partially overlapping in time with said pulses of said first beam.

21. The method of claim 20, wherein each of said pulses of said second beam has a duration of between about 0.3 milliseconds and about one millisecond, and wherein each of said pulses of said second beam has an energy density of about one Joule per square centimeter.

22. The method of claim 13, further comprising the step of directing a third beam of visible coherent radiation at the skin tissue, substantially coaxially and substantially simultaneously with said first beam.

* * * * *